United States Patent
Overbeck et al.

(10) Patent No.: US 7,480,035 B2
(45) Date of Patent: Jan. 20, 2009

(54) GLARE-DIRECTED IMAGING

(75) Inventors: James L. Overbeck, Ada, MI (US); Richard J. Van Andel, Grand Rapids, MI (US)

(73) Assignee: X-Rite, Inc., Grand Rapids, MI (US)

(*) Notice: Subject to any disclaimer, the term of this patent is extended or adjusted under 35 U.S.C. 154(b) by 134 days.

(21) Appl. No.: 11/321,108

(22) Filed: Dec. 29, 2005

(65) Prior Publication Data

US 2006/0103837 A1 May 18, 2006

Related U.S. Application Data

(62) Division of application No. 10/146,752, filed on May 16, 2002, now Pat. No. 7,006,210.

(60) Provisional application No. 60/291,446, filed on May 16, 2001.

(51) Int. Cl.
*G01B 11/26* (2006.01)
(52) U.S. Cl. ................. 356/138; 356/445
(58) Field of Classification Search ............ 356/138, 356/614, 620
See application file for complete search history.

(56) References Cited

U.S. PATENT DOCUMENTS

| | | | |
|---|---|---|---|
| 4,596,745 A * | 6/1986 | Chao | 428/428 |
| 4,989,984 A * | 2/1991 | Salinger | 356/445 |
| 5,155,558 A * | 10/1992 | Tannenbaum et al. | 356/446 |
| 5,608,527 A | 3/1997 | Valliant et al. | |
| 5,764,874 A | 6/1998 | White | |
| 5,963,328 A | 10/1999 | Yoshida et al. | |
| 6,031,620 A * | 2/2000 | Typpo | 356/445 |

(Continued)

FOREIGN PATENT DOCUMENTS

EP 0992763 4/2000

(Continued)

OTHER PUBLICATIONS

Zheng, Jiang Yu; "3D Surface Estimation and Model Construction from Specular Motion in Image Sequences", IEEE Transactions on Pattern Analysis and Machine Intelligence, May 1997.

(Continued)

*Primary Examiner*—Roy M Punnoose
(74) *Attorney, Agent, or Firm*—McCarter & English, LLP

(57) ABSTRACT

Imaging that uses glare to confirm proper measurement of a sample. An imaging device illuminates an object and generates glare (i.e., specular reflection, diffuse reflection or a combination of the two) off the object's surface, which is displayed on a display as a glare artifact. The location of the glare artifact is compared to a predetermined location to establish adjustment to obtain a desired angular orientation. The imaging device optionally highlights the glare artifact and steers a user to obtain the desired presentation angle. In two other embodiments, the spatial relationship between the imaging device and the object is time-varied. In one, the imaging device monitors changing glare and acquires a measurement when a desired glare is detected. In the other, the imaging device captures multiple images including varying glare artifacts and analyzes the images to select a preferred image having a glare artifact indicative of a desired angular orientation.

29 Claims, 11 Drawing Sheets

U.S. PATENT DOCUMENTS

| | | | |
|---|---|---|---|
| 6,088,116 | A | 7/2000 | Pfanstiehl |
| 6,222,628 | B1 | 4/2001 | Corallo et al. |
| 7,006,210 | B2 * | 2/2006 | Overbeck et al. ........... 356/138 |

FOREIGN PATENT DOCUMENTS

JP 06302674 10/1994

OTHER PUBLICATIONS

Garcia, Bermejo, J. Gomez; "Industrial Painting Inspection Using Specular Sharpness"; Proceedings of the International Conference on Recent Advances in 3-D Digital Imaging and Modeling, 1997.

Solomon, Fredric; "Extracting the Shape and Roughness of Specular Lobe Objects Using Four Light Photometric Stereo", IEEE Transactions on Pattern Analysis and Machine Intelligence, Apr. 1996.

Zheng, Jiang Yu; "Shape and Model from Specular Motion", Proceedings of the Fifth International Conference on Computer Vision, 1995.

Schultz, Howard; "Retrieving Shape Information from Multiple Images of a Specular Surface", IEEE Transactions on Pattern Analysis and Machine Intelligence, Feb. 1994.

Shrikhande, Neelima; "Surface Orientation from a Projected Grid", IEEE Transactions on Pattern Analysis and Machine Intelligence, Jun. 1989.

Sanderson, Arthur C.; "Structured Highlight Inspection of Specular Surfaces", IEEE Transactions on Pattern Analysis and Machine Intelligence, Jan. 1988.

* cited by examiner

GLARE-DIRECTED IMAGING

CROSS REFERENCE TO RELATED APPLICATIONS

This application is a division of U.S. patent application Ser. No. 10/146,752, filed May 16, 2002 now U.S. Pat. No. 7,006,210, and claims the benefit of U.S. Provisional Patent Application No. 60/291,446, filed May 16, 2001 and entitled GLARE POSITIONING TECHNIQUES FOR IMAGING OF SAMPLES WITH REFLECTANCE MEASURING INSTRUMENTATION.

BACKGROUND

The present invention relates to measuring characteristics of an object such as color, translucence, contrast, texture, roughness and the like. More particularly, the invention relates to optically measuring these characteristics for an object that generates glare when illuminated.

When an object having a smooth, glossy surface is illuminated with light, some of that light usually is reflected in a way that degrades viewing of the object, for example, by creating a bright white spot that appears to be emanating from the object. This bright spot is associated with an optical phenomena referred to as "glare."

Glare is generated by beams of light from an illumination source being reflected from an object's surface directly along an observation line of an observer, or an optical device, such as an imaging device or a camera. In most cases, glare is a reflected image of the light source itself. FIG. 1 illustrates the interaction of a light beam generated by illumination source 3 with a surface 10 to generate glare, i.e., reflected light beam 8, as viewed by observer O. Incident light beam 2, refracted light beam 4 and reflected light beam 8 interact with surface 10 under Snell's law, which provides that the angle A of incident light beam 2 is equal to the angle B of reflected light beam 8 as referenced to an axis 5 normal to the surface. Refracted light beam 4 interacts with the object. Portions of beam 4, when redirected by interaction to emerge from the object, may be observed by observer O along observation lines 6 to provide useful information, such as color, transparency, texture, etc., about the object. However, where the observer's observation lines 6 coincide with the reflected light beam 8, the observer can only perceive a bright spot appearing to emanate from the surface at point C. This bright spot is referred to as a glare artifact.

Although not a significant problem in casual human observation, glare provides many challenges in photographic and imaging applications because it detracts from captured images and eliminates useful information, e.g., color, contrast, translucency, etc., in locations coinciding with glare artifacts in the images. Accordingly, many conventional imaging devices are configured to manage reflected light beams, particularly light beams reflected from glossy or shiny surfaces, and prevent them from reaching the imaging device to generate glare artifacts in images.

A typical glare-eliminating imaging instrument, shown in FIG. 2, includes a directional light source 3 and an imaging device 12. These components are geometrically positioned to prevent the reflected light beams 8 from reflecting along an observation axis 14 of the imaging device 12, which is at a 45 degree angle from normal to the glossy surface 10. Specifically, the illumination source 3 is configured to project light beams 2 toward the glossy surface 10 along lines normal to the surface. Under Snell's law, the incident light beams 2 generate reflected light beams 8, which reflect toward the light source at an angle normal to the surface. Accordingly, the reflected light beams are not coincident with observation axis 14 nor observation lines 6, and therefore are not detected by the imaging device 12. Thus, no glare is seen by the instrument or generated in resulting images.

Another glare-reducing imaging instrument design uses polarized light to reduce glare artifacts. Specifically, an illumination source projects light polarized at one angle and an imaging device includes a filter to transmit light to the device at a different angle. Reflected light is cross-polarized out from any resulting image.

Although most conventional imaging processes attempt to reduce the impact of glare in captured images, a few actually use it, but only for limited purposes. For example, U.S. Pat. No. 6,222,628 to Corallo measures the intensity of glare from a sample to determine the roughness of a metal surface. In U.S. Pat. No. 5,764,874 to White, the intensity of glare is measured in regions of cigarette paper coated with glue and compared to the measured intensity of glare in regions not coated with glue to ensure that enough glue is applied to the paper. In another example, a specific type of glare-specular reflection from a glossy surface-is used to reconstruct a three-dimensional shape of an object from a two-dimensional image of the object. Specifically, the three-dimensional surface shape of an object is calculated by analyzing locations of specular reflection in either multiple images from multiple viewpoints under one light, or multiple images from a single viewpoint under a different light sources. H. Shultz, *Shape Information from Multiple Images of a Specular Surface*, IEEE Transactions on Pattern Analysis and Machine Intelligence, 16:195-201 (1994).

Until recently, conventional imaging devices have been designed to reduce the effect of glare on image capture. And even now, the intensity of glare is used only in specific applications to analyze attributes of glare-generating surfaces or extract three-dimensional information from two-dimensional images. Thus, many opportunities exist to exploit the information provided by glare.

SUMMARY OF THE INVENTION

The present invention is directed to a process of exploiting glare information to obtain a desired measurement of an object. More particularly, the invention uses glare information to assist a user in obtaining a desired orientation of an imaging device relative to an object to be measured.

In a preferred embodiment of the invention, glare information is relied on to adjust the angular orientation of an imaging device and an object measured relative to one another. More specifically, to satisfactorily measure a reflectance characteristic such as color, translucency, contrast, and related appearance variables including texture and gloss, a desired angular orientation, is acquired by positioning a glare artifact in a predefined location in an image of the object. To do so, the object is illuminated with a glare-generating light source. The image, including measured glare artifacts created by the illumination—typically indicated as bright white spots—is displayed on a display. By positioning the glare artifacts in a "predefined" or "ideal" location in the image, the imaging device is substantially reoriented until the desired angular orientation of the imaging device and object relative to one another is attained.

In a more preferred embodiment, the imaging device outlines or highlights measured glare artifacts and/or the ideal location of the glare artifacts on the display. Thus, a user can identify the measured glare artifacts and/or the ideal location of the artifacts to adjust the angular orientation of the imaging device until the measured artifacts register with the ideal locations in the image.

In an even more preferred embodiment, the imaging device "steers" the user, or an associated image device holding mechanism, to adjust the imaging device to the desired angular orientation. The imaging device analyzes an image of an object to determine the measured locations of glare artifacts in the image. These measured locations are compared to ideal locations of the glare artifacts. If the comparison indicates that the measured and ideal locations do not coincide, then the imaging device computes a steering function corresponding to the change in the angular orientation necessary to relocate the measured location near or coincident with the ideal location. The steering function preferably is displayed on the display to steer the user in repositioning the imaging device. Where the imaging device is supported on a holding mechanism, the steering function is used to control the mechanism and adjust the imaging device.

In a second embodiment, the imaging device monitors the changing glare information of a passing object to determine when the object is in a desired orientation for acquiring an image including a satisfactory measurement of reflectance characteristics. For example, in a conveyance line, an imaging device determines the orientation of an object as its relationship to the imaging device changes based on the position of glare artifacts associated with the object. When the imaging device determines that the glare artifact is in a location that is indicative of a desired angular orientation, the imaging device captures an image of the object.

In a third embodiment, the imaging device captures multiple images of a passing object. A user or the imaging device selects those images with glare information positioned in preferred regions of the image that coincide with desired illumination or a desired angular orientation of the imaging device and object relative to one another. Measurements may be taken from regions of interest in the selected images with confidence that the illumination or angular orientation was satisfactory.

In a fourth embodiment, an imaging device is provided that includes multiple, glare-generating illumination sources. When an object is illuminated with these sources, and imaged by the imaging device, the resulting image includes multiple measured glare artifacts. By reconciling the measured glare artifacts with corresponding ideal glare artifact locations, it is possible to determine with increased confidence that the imaging device and measured object were in a desired angular orientation when the image was acquired.

In a fifth embodiment, the imaging device includes one or more time-varying illumination sources that produce multiple, different glare artifacts in images captured by the imaging device. By reconciling these many glare artifacts with corresponding ideal glare artifact locations, it is possible to ensure the desired angular orientation is achieved during measurement.

The present invention offers many benefits. First, the invention uses glare information to assist a user in obtaining a desired angular orientation of an imaging device relative to a measured object. This, in turn ensures that a captured measurement or image contains useful data. Second, the imaging device of the invention can identify glare artifacts in an image for a user to assist the user in adjusting the device. This is useful when imaging glossy objects, and even more useful when imaging matte-finish objects, which typically do not generate well-defined glare artifacts. Third, with time-varied positioning of imaged objects, glare information is effectively used to determine when an object is properly illuminated or the device is properly oriented to subsequently acquire useful measurements or images of the object. Fourth, when multiple images of a moving object are captured, glare information may be used to select useful measurements or images. Fifth, with multiple illumination sources or time-varied illumination sources, it is possible to generate more glare artifacts which may be reconciled with corresponding, ideal glare artifact locations to confirm with a high degree of confidence that desired angular orientation is achieved.

These and other objects, advantages and features of the invention will be more readily understood and appreciated by reference to the detailed description of the invention and the drawings.

DETAILED DESCRIPTION OF THE INVENTION

I. Overview

Figure 1:
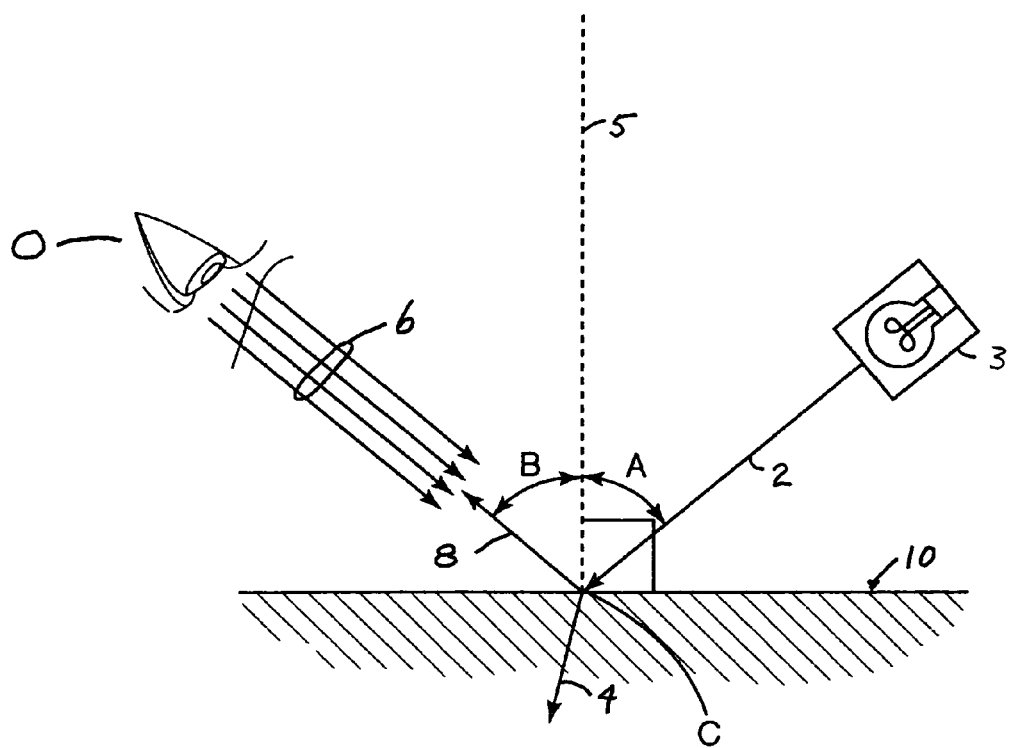
FIG. 1 is a side elevational view of observation of specular reflection in the prior art.
Figure 2:
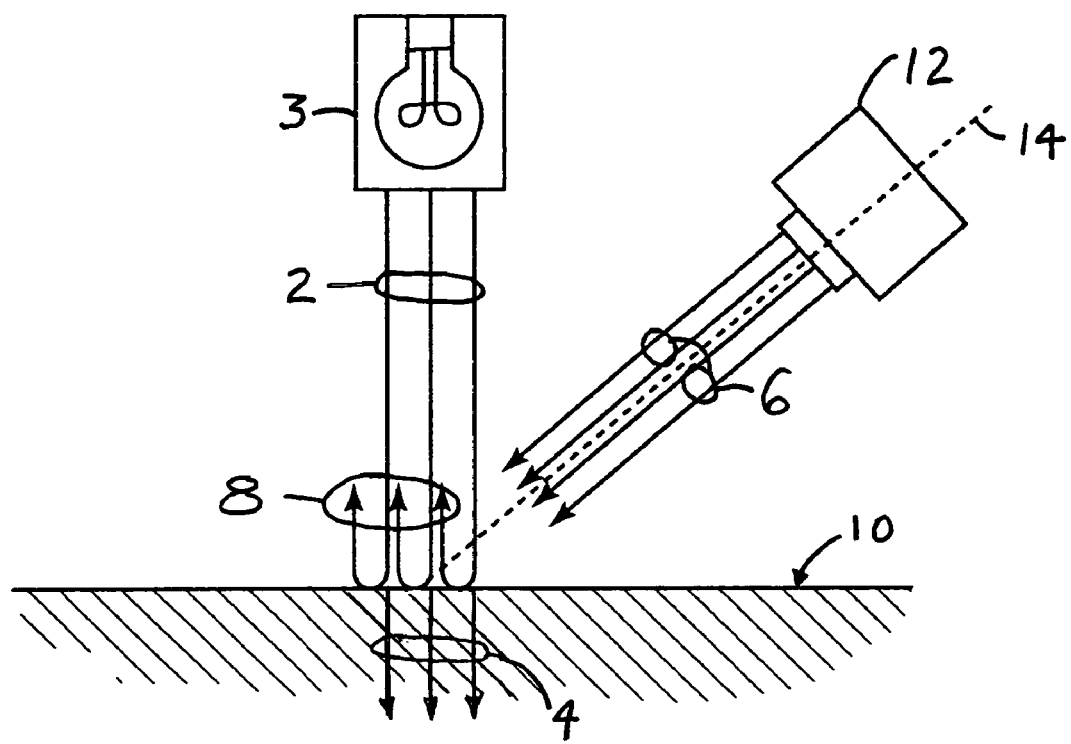
FIG. 2 is a side elevational view of a specular reflection-eliminating imaging device of the prior art.
Figures 3, 3A:
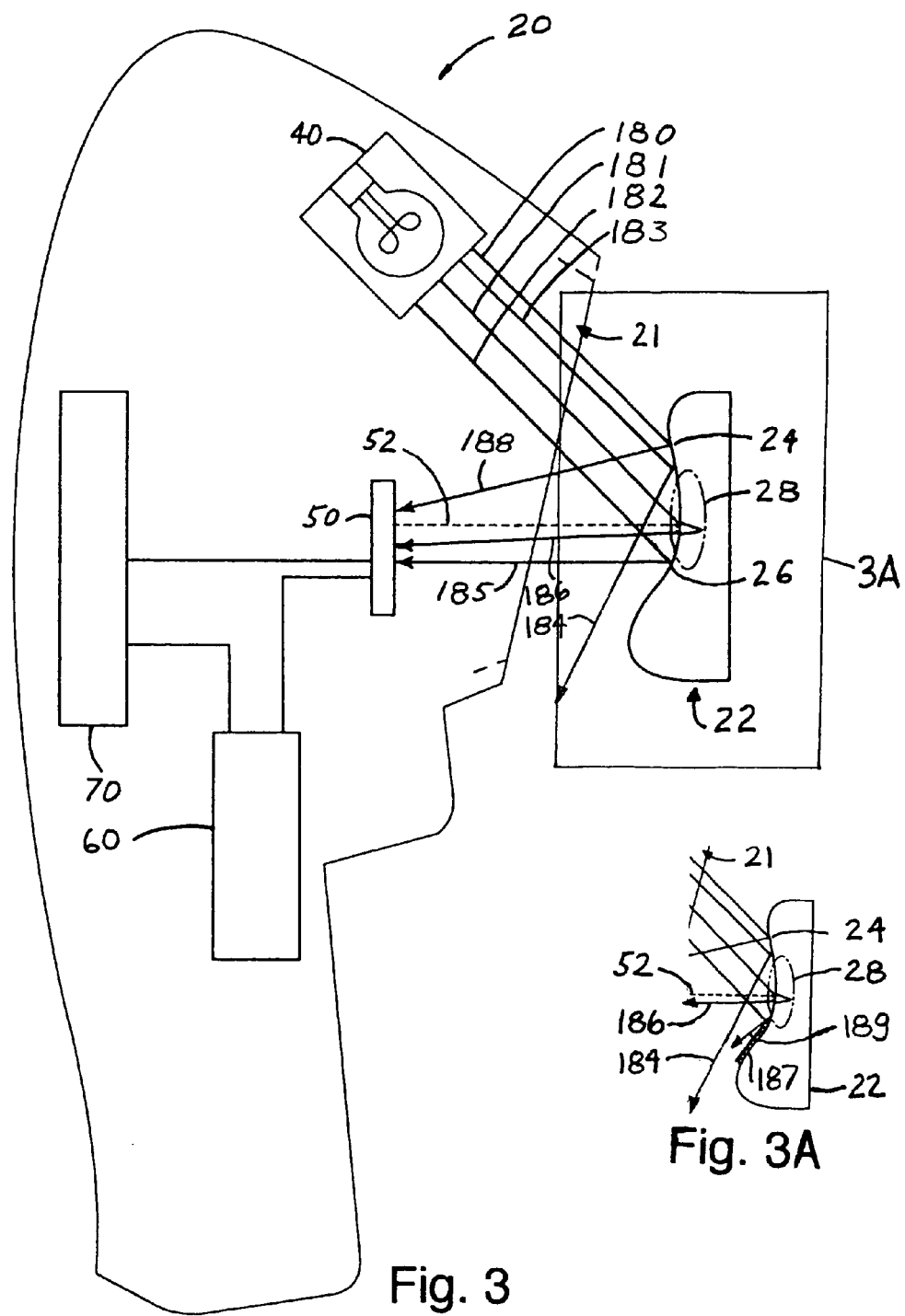
FIG. 3 is a side elevational view of the imaging device of the present invention measuring a sample.
FIG. 3A is a detail view of an illuminated sample including a diffuse specular reflection.

An imaging device constructed in accordance with a preferred embodiment of the invention as illustrated in the drawings and generally designated 20. Major components of the imaging device are illustrated in FIG. 3 and include an illumination source 40, an image sensor 50, a processor 60 and a display 70. Although the imaging device is depicted as a portable instrument, it may also be stationary with the independent components mounted in relation to a sample as desired.

The illumination source 40 illuminates a sample 22 and the image sensor 50 captures images through the viewing port 21. The image sensor 50 is in communication with the display 70, and the display displays captured information as an image. Both the display 70 and the image sensor 50 may be in further communication with a processor 60 that analyzes the information captured by the image sensor 50 and displayed on the display 70.

Figure 4:
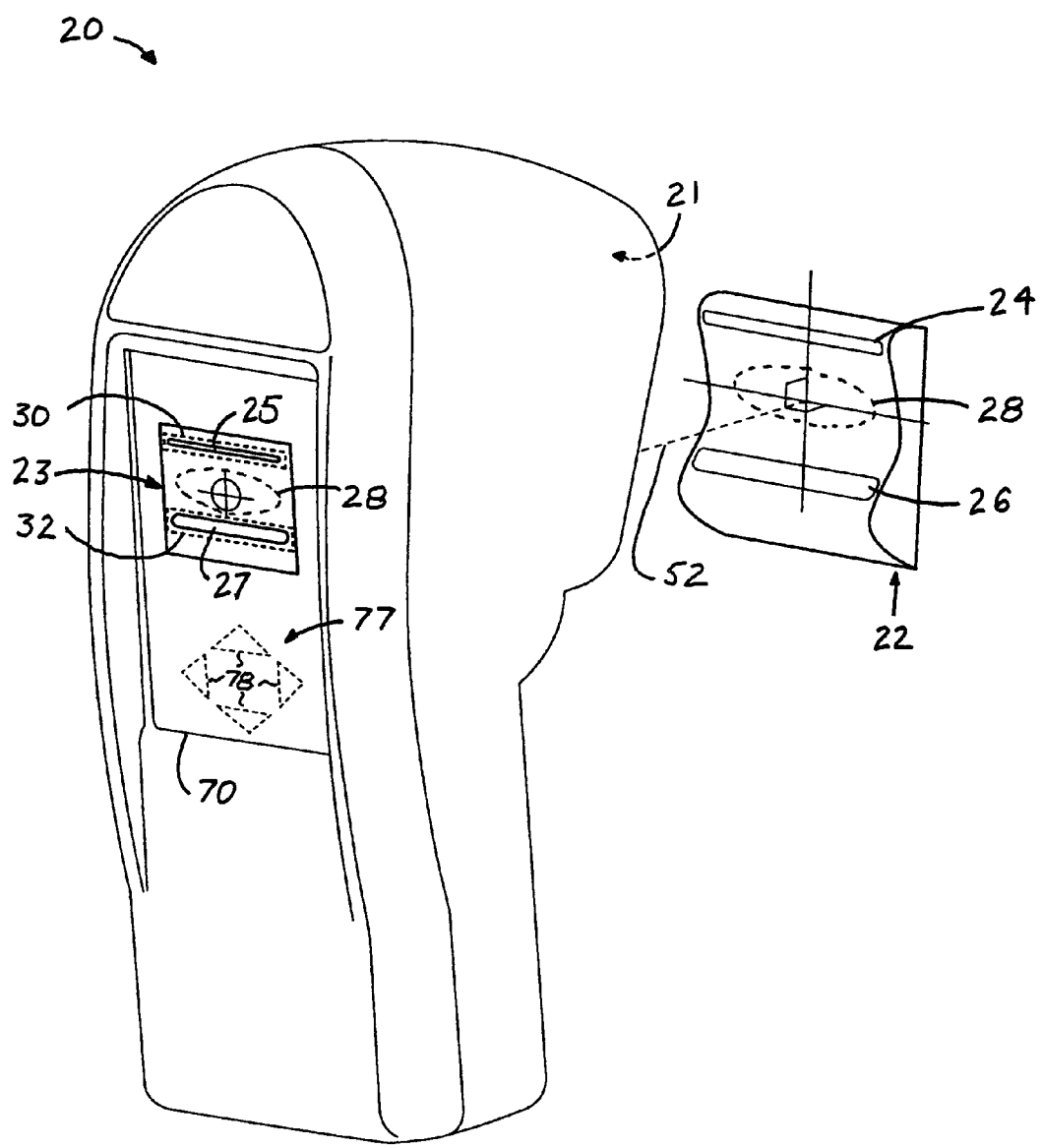
FIG. 4 is a perspective view of the imaging device measuring and displaying a sample.

In use as shown in FIGS. 3 and 4, a sample 22 is placed adjacent the viewing port 21. Light from illumination source 40, that is, incident rays 180-183, passes out the viewing port 21 to impinge on the sample 22. Many rays are reflected from the surface of the sample 22, including reflected specular rays 184, 185 and 188. Some of the specular reflected rays, for example, 188 and 185, are directed back along the optical axis 52 of the image sensor 50. Other rays, for example diffuse reflected ray 186, also are directed toward the image sensor 50 for capture and later use in reflectance measurement (described below). Other reflected rays, such as reflected specular ray 184, are reflected away from the image sensor. The image sensor captures an image of the sample 22 in the perspective perceived by the image sensor, including the reflected rays 188, 185 and 186 and a region of interest 28. In the areas from which reflected specular rays 188 and 185, are reflected toward the image sensor, glare artifacts 24 and 26 are generated. These artifacts are also captured by the sensor.

Where the sample 22 also includes a matte-finish surface, for example in region 189 shown in FIG. 3A, the rays reflected from the sample may further include diffuse specular ray 187, which may or may not be reflected toward and captured by the image sensor 50.

The image sensor transfers information to the display 70, which displays an image 23 of the sample. The image includes image glare artifacts 25 and 27 corresponding to glare artifacts 24 and 26 of the sample from which rays 180 and 185 are reflected. The image produced on the display 70 can be viewed to determine whether the imaging device 20 is properly oriented relative to the sample, preferably so that the optical axis 52 of the image sensor is normal to the surface of the sample in the region of interest 28.

Predefined locations 30 and 32, either known to the user or provided on the display 70, are used to guide orientation of the imaging device. Specifically, when the glare artifacts 25 and 27 are substantially coincident with the regions 30 and 32, respectively, the user can confirm that the imaging device is in the desired angular orientation.

With the desired angular orientation of the imaging device 20 relative to the region of interest 28 established, a user may be confident that the region is properly captured in image 23. Accordingly, that region and the reflectance characteristics of the sample 22 in the region 28 or other regions, if desired, may be analyzed. "Reflectance characteristics" refers to any of the following, alone or in combination: color, translucence, contrast, and related appearance variables including relative gloss value, texture and roughness.

Reference in this application is made to the terms "specular reflection," "diffuse reflection," "diffuse specular reflection," "glare" and "glare artifact." As used herein, "diffuse reflection" refers to light that has penetrated into an object, is scattered within it and emerges, in part at an angle that is captured by a image sensor, camera, or observed by a viewer. "Specular reflection" means light that has only interacted with the surface of the object and is reflected in whole or part at an angle that is captured by an image sensor, camera, or observed by a viewer. An example of a specular reflection is the redirection of light that occurs on the surface of a smooth metal. A specular reflection can appear to be diffuse, for example, when it is redirected from the surface of matte metal finish. To differentiate this phenomenon, such specular reflections that appear diffuse are referred to herein as "diffuse specular reflections." "Glare" means specular reflection or diffuse specular reflection or any combination of specular reflection, diffuse specular reflection and diffuse reflection of an area where the resulting reflection is detectably greater than the diffuse reflection of a surrounding area. "Glare artifact" means the portion or area or region of an object or an image of an object that appears to emanate or emanates glare.

II. Components of the Imaging Device

The overall physical construction of the imaging device as depicted in FIG. 3 and including the illumination source 40, image sensor 50, microprocessor 60 and display 70, will now be described in detail.

The illumination source 40 preferably is adapted to generate glare when it illuminates an object. More preferably, the illumination source 40 is adapted to both provide sufficient illumination to measure an object and generate glare from the object. In the most preferred embodiment, the source 40 is a directional illumination source that produces a substantially collimated beam of light. Optionally, two illumination sources (not shown) may be used, where one generates glare and the other illuminates the object for measurement. Additional sources may be added to perform either function. Examples of other glare-generating illumination sources that may be include, for example, a light-emitting diode or an illumination source that projects a focused or semi-focused beam of light. Illumination source 40 preferably provides light within the visible spectrum; however, it may provide light at some wavelength that is not visible in the region of interest 28 or the displayed image 23, as desired. For example, the illumination provided may be of near-infrared, infrared or ultraviolet bandwidths.

Optionally, the illumination source 40 is switched-off during acquisition of an image or measurement of the sample 22 (described below). This is acceptable where a secondary illumination source (not shown) is used to illuminate the sample 22 or region of interest 28 on the sample. Turning-off the directional illumination source 40 during image or measurement capture reduces or eliminates glare artifacts 25 and 27 from the image 23 of the sample.

In the embodiment shown in FIG. 3, the illumination source 40 is at a 0/45° geometry relative to the image sensor. Specifically, the illumination axis 41 of the illumination source 40 is at a 45° angle relative to the optical axis 52 of the imaging sensor 50. In an ideal measuring environment of region 28, the optical axis 52 is normal to substantially all points in the region of interest 28. Optionally, a variety of other geometries may be used, for example, a 45°/0 geometry, a 25°/0 geometry, a 0/25° geometry, or any other geometry conducive to measuring reflectance characteristics.

The image sensor 50 of the imaging device includes an observation axis 52, also referred to as an optical axis, which is normal to the surface of the sensor. In most measuring situations, it is desirable to orient this optical axis at a particular angle relative to the region of interest. Such orientation is referred to as the "angular orientation" of the image sensor and/or imaging device. In many cases, it is desirable that the angular orientation of the imaging device is such that the optical axis of the image sensor is substantially normal to the region of interest; however, depending on the surface or characteristics to be measured, other angles may be selected.

The image sensor preferably is a charge coupling device (CCD) capable of detecting color. Other image sensors, such as monochromatic complimentary metal-oxide semiconductors (CMOS) may be substituted for the CCD as desired. Optics may be employed as necessary to form an image of the sample on the image sensor. Further, spectrally selective optical elements may be added to the device 20 as desired, for example bandpass filters and the like. Moreover, the spectral bandpass function measured by the image sensor may be modified or additional components added to obtain a desirable measurement. As a general example, the image sensor may be spectrally selective, that is, it may act as a spectrophotometer, a colorimeter, or a densitometer when modified or combined with other components. As a more specific example, the image sensor may be a monochrome image sensor used in conjunction with tailored illumination and broadband filters in an imaging colorimeter to provide a desired measurement. Optionally, the image sensor may be replaced with a conventional photographic camera.

The image sensor is in communication with the display 70 so that information may be transferred from the image sensor to the display 70 for output of an image 23 on the display. Preferably, the display is a liquid crystal display capable of displaying the captured image in color; however, a monochromatic display may also be used. The image 23 of the sample 22 is preferably a live video feed to the display 70, however, the image 23 may be a still video image in some applications.

The display may further include an information field 77 that provides text or graphical instructions to a user. As shown in FIG. 4, the display includes arrows 78 (in an inactivated state), which indicate the direction that the imaging device 20 must be adjusted to obtain a desired angular orientation relative to the sample 22. Optionally, the information field 77 may be disposed around the perimeter of the display 70 with the arrows 78 disposed on each of the sides of the display perimeter 77, or any other configuration that facilitates understanding of information conveyed by the display.

The display also is adapted to generate highlighting areas 30 and 32 in an image of the sample 23 which corresponds to the glare artifacts as captured by the image sensor. The highlighted areas 30 and 32 may alternatively or additionally correspond to the ideal positions of the glare artifacts within the image to obtain a desired angular orientation of the device 20. The number, shape, orientation and highlighting may vary depending on the image captured or the desired settings of the user. For example, as shown, the highlighted areas 30 and 32 are depicted as broken lines. Optionally, the highlighted areas may be indicated in full lines outlining the glare artifacts 25 and 27. Alternatively, the highlighted areas 30 and 32 may be shaded or colored completely within the boundaries thereof and coincident with the artifacts 25 and 27.

The imaging device 20 further includes a processor 60 in communication with the image sensor 50 and display 70. Optionally, where a smaller, portable imaging device is needed, or where large processors are required to make complex computations, the processor may be external to the imaging device. In such situations, communication between the processor and other components of the imaging device may be established via direct electrical or conventional remote communication systems.

The processor of the current embodiment includes sufficient memory to store predefined, or "preferred," or "ideal" locations of glare artifacts within an image of a sample to attain desired angular orientation of the imaging device. The processor further includes sufficient processing capabilities to generate on the display 70 instructions to adjust the angular orientation of the imaging device 20 and align glare artifacts 25 and 27 with locations 30 and 32. This provision of instructions is generally referred to as "steering" the user. As will be appreciated, in embodiments where the imaging device 20 is held by a fixture or machine, for example, a robot, the processor can provide sufficient instructions to the robot to reorient the imaging device and establish the desired angular orientation.

Further, the processor includes sufficient memory to store multiple captured images of samples and the information associated with those images. The processor optionally may include a communication means for downloading images stored in the memory of the processor or allowing simultaneous viewing of the image on the display 70 on another display (not shown). Suitable communication means include, but are not limited to: USB connections; wireless connections; high-data transfer speed connections (e.g., connections available under the common name, "Fire-Wire"); and connections available under the common name "Ethernet." The processor should further include sufficient processing capabilities to carry out the operations of the imaging device in use as explained in detail below.

III. Operation and Method of Use

The present invention enables a user to attain a desired angular orientation of an imaging device 20 relative to a region of interest on a sample to properly measure reflectance characteristics associated with that region.

Figure 5:
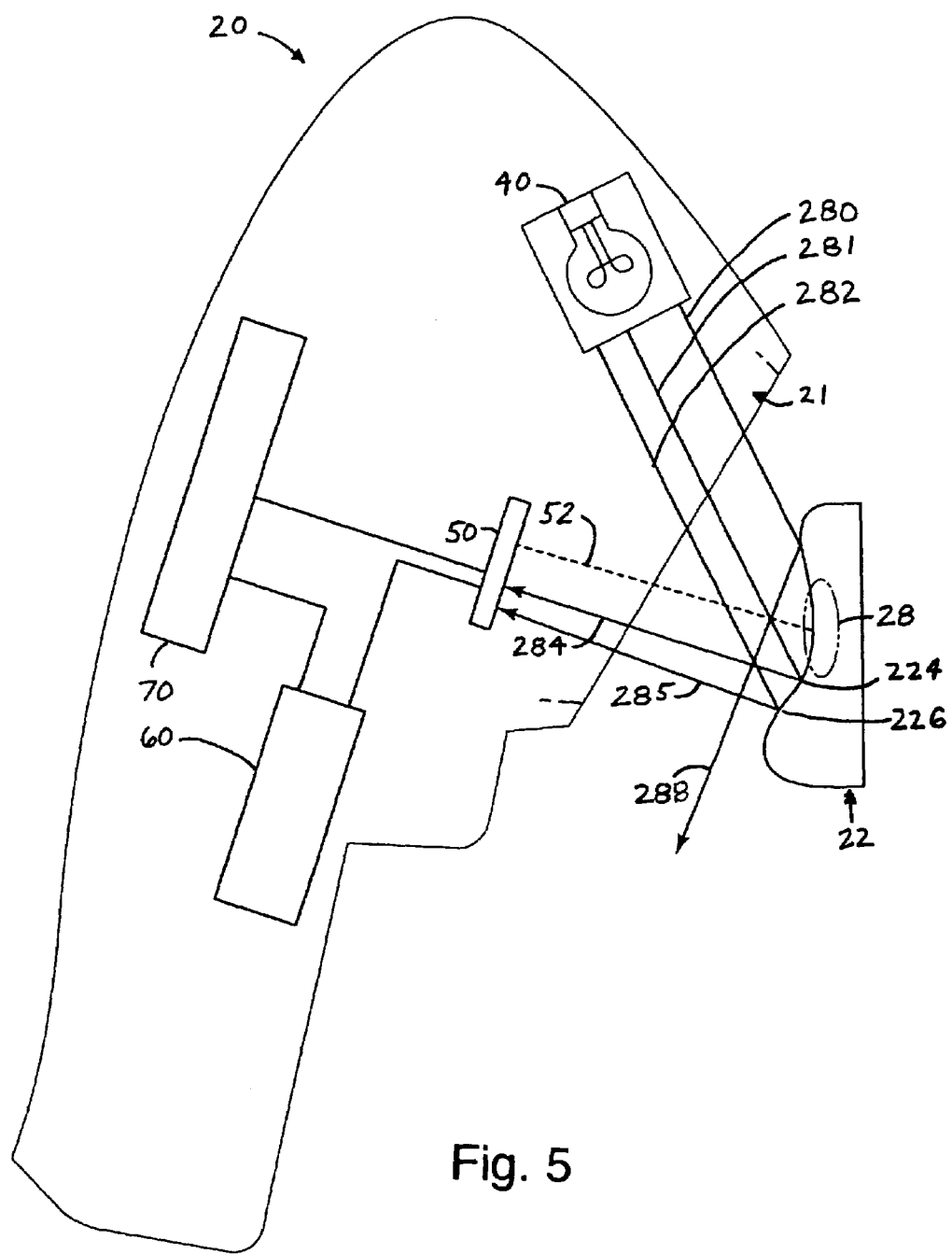
FIG. 5 is a side elevational view of the imaging device in a pre-measurement orientation.
Figure 6:
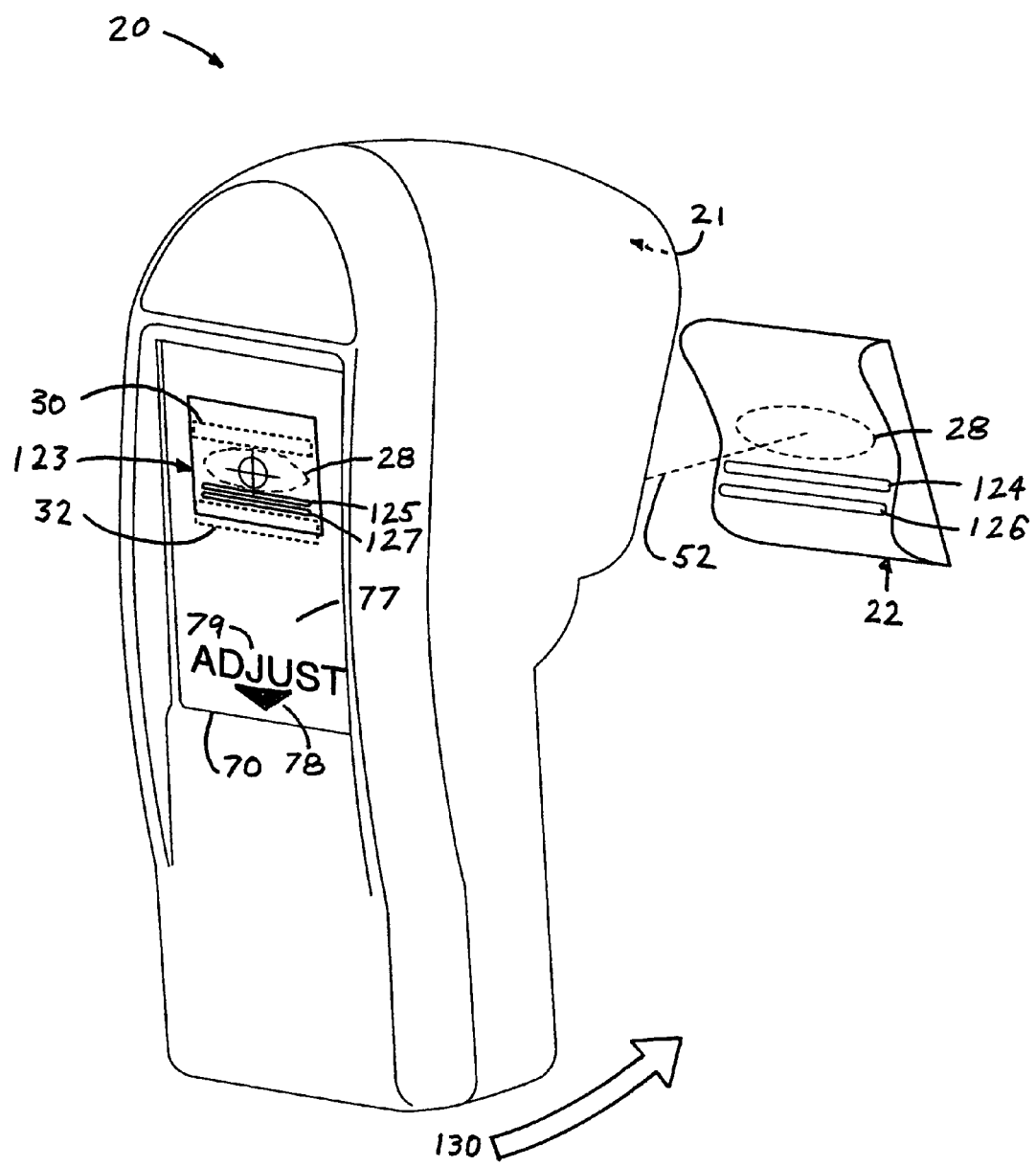
FIG. 6 is a perspective view of the imaging device in the pre-measurement orientation.
Figure 7:
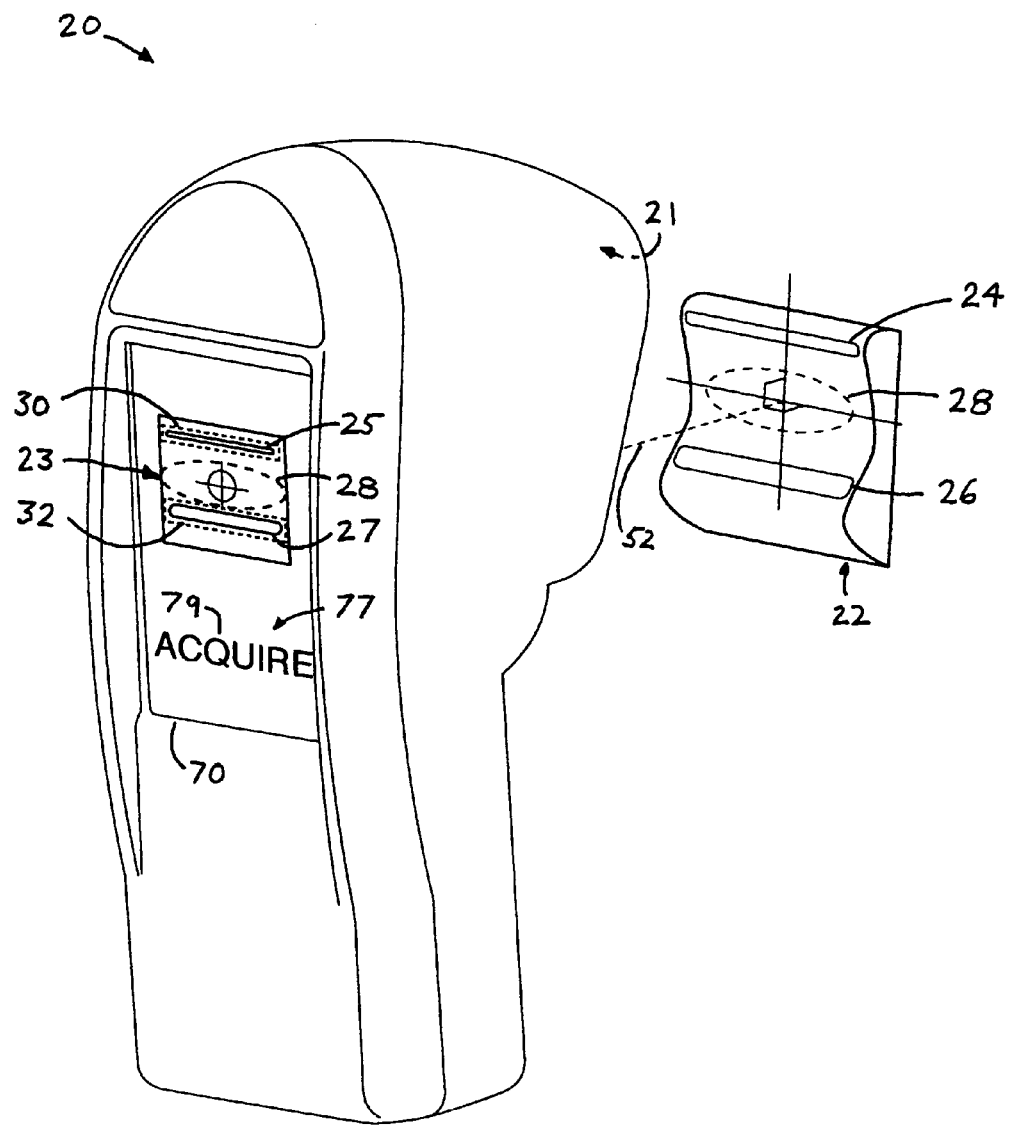
FIG. 7 is a perspective view of the imaging device in a measuring orientation.

With reference to FIGS. 5-7 there will now be described a preferred process of the present invention. As a first step in the process, a user disposes the imaging device 20 adjacent a region of interest 28 on the sample 22 that the user wants to measure. The user generally attempts to ensure that the sample 22 is within the field of view of the image sensor 50, so that an image 123 of the sample is displayed on the display 70. As will be appreciated, the image 123 is displayed in the perspective in which the image sensor sees the sample. As the image 123 is displayed, the illumination source 40 is activated either automatically by the device or manually by the user, to impinge incident rays 280-282 onto the surfaces of the sample 22. As shown in FIG. 5, this results in rays 281 and 282 being reflected directly off the surface of the sample in areas 224, 226, as reflected rays 284 and 285, which are directed back along the optical axis 52 of the image sensor. Accordingly, these regions 224 and 226 are represented as glare artifacts 125 and 127 in the resulting image 123. Optionally, the glare artifacts 125 and 127 may be highlighted as desired if they are not well-defined on the display. For example, the measured glare artifacts may be outlined or colored differently on the display 70. If the sample 22 is brightly colored, the contrast difference of the glare artifacts 125 and 127 may be enhanced, or alternatively, the lightness or color of those artifacts 125 and 127 may be changed to an artificial value to further call out the artifacts for the user.

As the image of the sample 123 is displayed with measured glare artifacts 125 and 127 associated with it, the processor analyzes the position of those glare artifacts. Specifically, the processor defines the boundaries or perimeter of the sample in the image using techniques known in the art. The processor generates relationships between the perimeter and the location of the measured glare artifacts 125 and 127 in the image to identify where, in the area bound by the image sample 123, the artifacts are located. With the location of the measured artifacts 125 and 127 defined, the processor compares those locations to preferred locations of the artifacts 30 and 32, which are highlighted on the display as shown, but need not be highlighted in actual use. These preferred locations of the artifacts also referred to as predetermined locations or ideal locations and may be determined in a variety of ways as explained in further detail below.

Based on the comparison, the processor generates a steering function that represents the adjustment of the angular orientation of the imaging device (i.e., adjustment of the optical axis 52 of the image sensor relative to region 28) necessary to move the measured glare artifacts 125 and 127 so that they register or coincide with the preferred locations 30 and 32. As shown in FIG. 6, the steering function may be output in the information field as highlighted arrow 78 with optional text 79 to instruct the user to adjust the imaging device in the direction indicated. Assuming the user desires to obtain a measurement of the region of interest 28 with the imaging device in an ideal angular orientation, the user subsequently adjusts the angular orientation of the imaging device 20 relative to the sample in the direction of the arrow 130. As will be appreciated, if a mechanical apparatus, such as a robot, is used to position the imaging device, the processor may instruct the robot to carry out the steering function and adjust the angular orientation of the imaging device.

It will be appreciated that steering need not be implemented if a user knows the position of the preferred glare artifact location. In such a situation, the user intuitively adjusts the device until the measured glare artifacts 124 and 126 are positioned in the user-known, predefined locations.

In the current embodiment where steering is used, throughout the adjustment of the angular orientation of the imaging device 20, the image of the sample 22 on the display 70 is updated. The user may watch as the glare artifacts 125 and 127 change in relation to the surface of the displayed sample 123. Ideally, the user stops adjusting the imaging device when the display no longer outputs adjustment arrows 78, or when the measured glare artifacts 25 and 27 coincide with preferred glare artifact locations 30 and 32 as shown in FIG. 7.

FIG. 7 depicts the imaging device immediately after the angular orientation of the instrument 20 is adjusted by the user to achieve an angular orientation wherein the optical axis 52 of the image sensor is normal to the region of interest 28. This orientation may be confirmed by observing the measured glare artifacts 25 and 27 displayed in the image 23 in registration with the preferred glare artifact locations 30 and 32.

At this point, the user captures the image of the sample 23. Optionally, the preferred glare artifact locations 30 and 32 may be highlighted during image capture on the display to assist the user in steadying the instrument. Moreover, the information field 77 of the display 70 may display text 79 to instruct the user to acquire the image.

Figures 8, 8A:
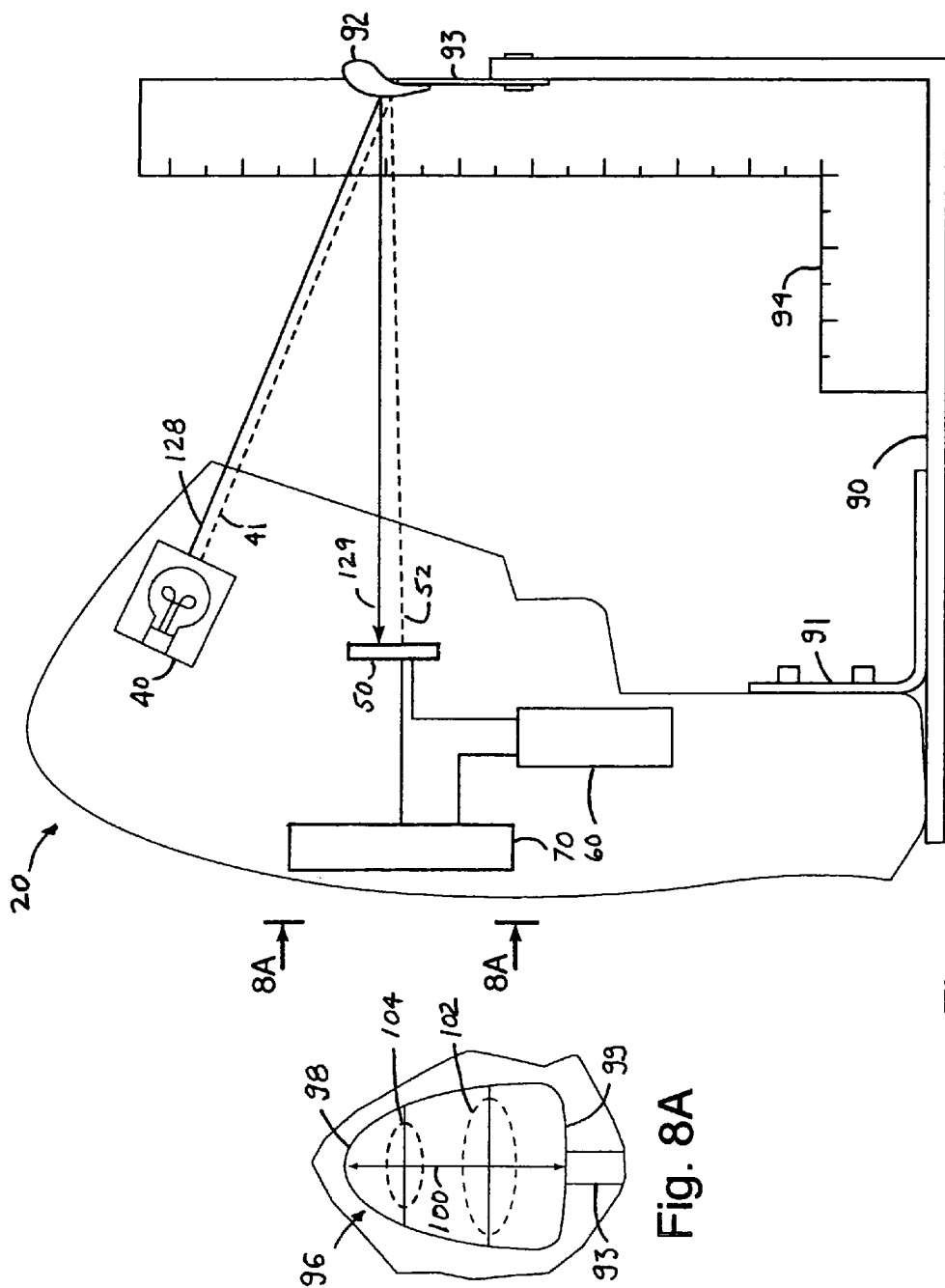
FIG. 8 is a side elevational view of the imaging device held in a fixture to study glare and an angular orientation.
FIG. 8A is a display of a commercially available shade tab reference.

With reference to FIGS. 8 and 8A, there will now be described a preferred technique to study the ideal locations of glare artifacts in an image and establish an adjustment protocol to attain a desired angular orientation for a specific object or class of objects. This example uses an experimental process for determining the ideal locations of glare artifacts. Although the example is disclosed in relation to the measurement of color and translucence of teeth to create dental restorations, it will be appreciated that it is also applicable to virtually any application requiring measurement of an object with accuracy or consistency.

The shape of the teeth can vary greatly, however, most teeth have convex curved surfaces with a decreasing radius of curvature close to the gum line which corresponds to the cervical edge of the tooth. Teeth tend to have the flattest surfaces in a central region of the tooth. Moreover, the central region of the tooth generally represents the overall color of the tooth, and if restorations are constructed to match this central region, then the restoration generally matches the natural tooth. Thus, it is desirable to obtain proper measurements of the central region of the tooth.

With reference to FIG. 8, this is accomplished by assuring that the optical axis 52 of the image sensor 50 is normal to that region during measurement. With imaging device 20 mounted in the fixture 90, the ideal location of glare artifacts within images of shade guides, and teeth in general, was established to ensure consistent angular orientation of the imaging device relative to teeth during measurements. The imaging device 20 shown in FIG. 8 includes the same components as the imaging device described above, however, the measuring geometry of the imaging sensor relative to the illumination source is 0/18°. This means that the optical axis during measurement is normal to the measured region of interest and the axis of illumination 41 is disposed at an angle D which is 18° from the optical axis 52. The imaging device 20 may optionally be outfitted with an optional spacing device (not shown) that spaces the shade guide 92 a pre-specified distance from the image sensor to ensure consistent lighting of the shade guide 92. 21 The imaging device 20 is mounted in fixed relation to the fixture 90 with mounting bracket 91. A shade guide tab 92 likewise is mounted to the fixture with a mount 93 in fixed relation to the fixture 90. A carpenter square 94, or other practical means is further associated with the fixture 90 to establish a normal relation between the points of the shade guide corresponding to the central location of the tooth 102 (FIG. 8A) and the optical axis 52 of the image sensor. In an experimental measuring sequence, the position of the glare artifact created by incident light 128, reflecting off shade guide tab 92 as reflected ray 129, was analyzed to determine the ideal location of glare artifacts in an image of a tooth. It was found that to ensure the optical axis 52 is normal to the central region 102 of the tooth, the glare artifact should be positioned in area 104, as shown in FIG. 8A, which is a display of the imaged shade guide 96 on display 70. Specifically, when the glare artifact is positioned on a shade guide, or tooth, in region 104, a user can be reasonably certain that the optical axis 52 of the image sensor 50 is normal to the central region of the tooth 102, which is region of interest in most applications. Region 104 is centered on a point about one-third of the distance 100 from the cervical edge 98 of the tooth to the incisal edge 99 of a tooth.

Testing may be conducted to confirm that the experimentally determined, ideal locations of glare artifacts are able to assist in angular orientation during an actual measuring scenario. Regarding the above experimentally determined ideal glare artifact locations for dental measurements, several tests were conducted to this effect. In one test, untrained operators used the imaging device to measure color and appearance variables of human teeth. To do so, they were told to activate the imaging device and illuminate the tooth. They were instructed to view the display and manipulate the imaging device so that glare artifacts created by the illumination was centered on a point about one-third the distance from the cervical edge of the tooth to the incisal edge of the tooth. The operators then captured measurement of the tooth. Upon analysis of the measurement data, it was determined that such positioning of the glare artifacts within an image of the tooth caused the instrument to function correctly. Specifically, the data suggested that the optical axis of the image sensor of the imaging device was normal to the central region of the tooth during measurement.

In other testing of the experimentally determined ideal glare artifact locations for dental measurements, an operator trained in proper angular orientation measured a tooth without regard to the position of the glare artifact in the image. Upon analysis of the measurement taken at the angular orientation specified by the trained observer, it was confirmed that the ideal glare artifact location was in a region about one-third the distance from the cervical edge of the tooth to the incisal edge of the tooth.

Thus, with the confirmatory testing methods above, ideal glare artifact locations may be confirmed so that users may reliably establish an angular orientation of an imaging device relative to an object to obtain useful measurement of that object. In the case of dental measurement imaging devices, this is particularly helpful because the angular orientation may be established in a freehanded manner that otherwise would require the use of a fixture.

An alternative to the experimental technique described above uses commercially available three-dimensional computer aided drafting (3D-CAD) or photo-rendering software to determine the location of glare artifacts that are characteristic of an ideal angular orientation of an imaging device relative to an object. In the first step of such a process, the angular orientation of a real imaging device to a real object is determined. For example, an ideal angular orientation of a real imaging device to a real object may be such that the optical axis of an image sensor of the real imaging device is normal to a specific surface of the real object.

Using a commercially available 3D-CAD for photo-rendering software package, for example, Pro/ENGINEER available from Parametric Technologies Corporation of Needham, Mass., a three-dimensional model of the real object is created or imported. Within the 3D-CAD or photo-rendering software package, the modeled object is oriented to mimic the view direction of the real imaging device in the ideal angular relation determined above. For example, the modeled object is oriented to replicate the real object as if it were imaged by the real imaging device in the ideal angular orientation.

In another step, the 3D-CAD or photo-rendering software package is used to create a directional lighting specification that matches or approximately matches the directional lighting expected when the real imaging device measures the real object. In yet another step, the 3D-CAD or photo-rendering software package renders or artificially shades the modeled object in accordance with the created directional lighting specification and the determined ideal angular orientation specified in the first step. The image rendered will show the preferred glare artifact locations within the rendered image that are characteristic of the ideal angular orientation as viewed by the real imaging device during actual measurement.

As will be appreciated, other techniques may be used to determine the preferred locations of glare artifacts characteristic of ideal angular orientations of the imaging device and the measured object relative to one another.

IV. First Alternative Embodiment

Figure 9:
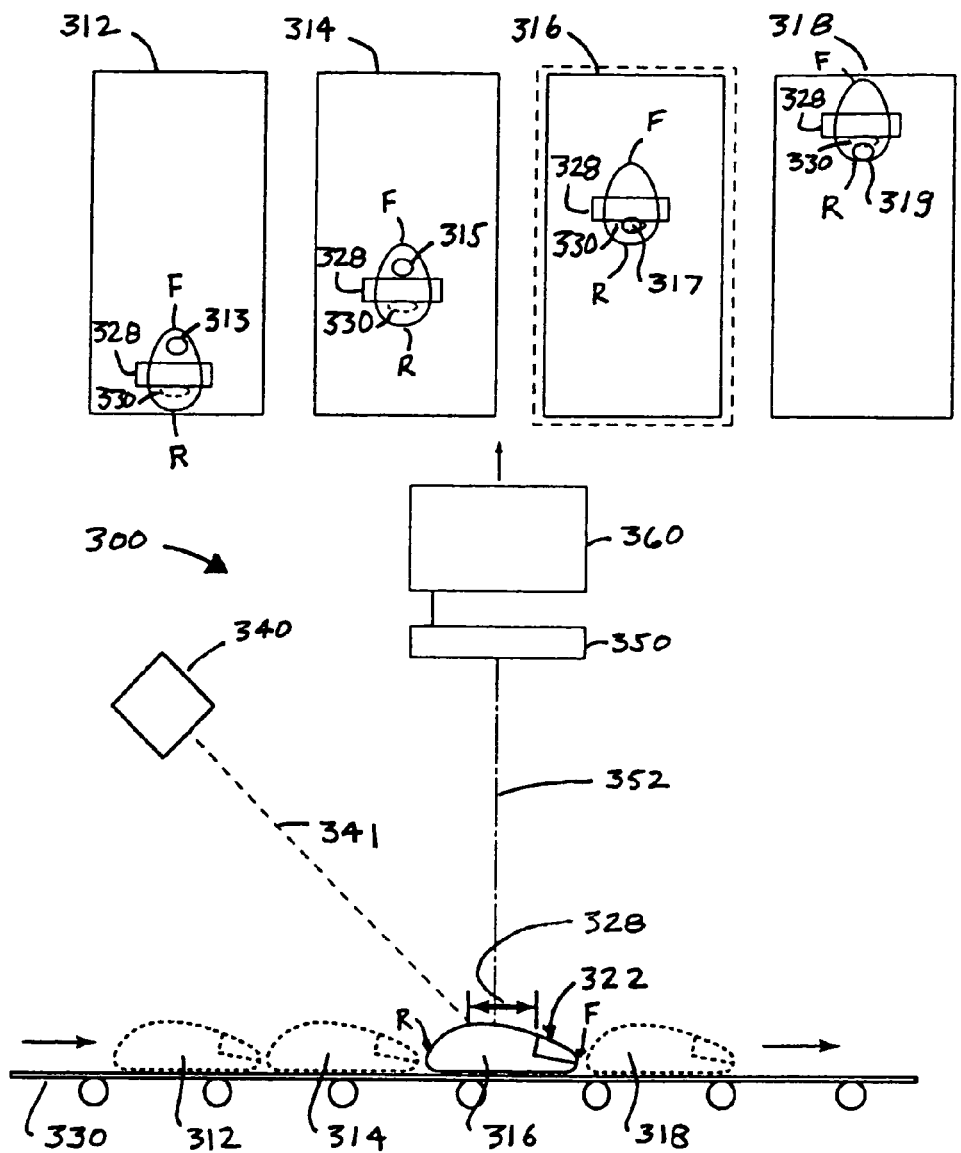
FIG. 9 is a side elevational view and output view of first and second alternative embodiments of the present invention.

An alternative embodiment 300 of the present invention is illustrated in FIG. 9. The imaging device 300 includes an image sensor 350 having an optical axis 352, a directional illumination source 340 and a processor 360 as described above. The imaging device 300 is mounted in relation to a conveyor system 330 that moves product 322 past the imaging device 300 in a time varying manner. This set-up may be used in an inspection station on a production line to ensure consistency of product, for example, homogeneous and consistent color.

As shown, the sample 322 is a computer mouse that is moved relative to the optical axis 352 and illumination axis 341 of the imaging device 300 through positions 312, 314, 316 and 318. The sample 322 has a region of interest 328 for which measurement of reflectance characteristics is desired.

In this embodiment, as the conveyor 330 conveys the sample 322 past the imaging device 300, the imaging device monitors the position of the glare artifact generated by light reflected from the surface of the sample 322. More specifically, as the sample 322 traverses positions 312, 314, 316 and 318, the image sensor detects the position of sample 322 in the image sensor's field of view. The sensor 350 further senses the relative position of the glare artifact created by light rays from illumination source 340 reflecting off the surface of the sample 322. The field of views of the image sensor as the sample moves are shown in scenes 312, 314, 316 and 318. The processor 360 monitors the relationship between the glare artifacts 313, 315, 317 and 319 and the preferred glare artifact location 330. The preferred glare artifact location 330 corresponds to an ideal position of the sample 322 relative to the optical axis 352 for capturing a useable image of the region of interest 328. Only when an acceptable orientation of the glare artifact, specifically, when the glare artifact 317 substantially registers with preferred location 330, does the image sensor capture an image of the sample 322. Scene 316 depicts that acceptable orientation and is outlined to indicate that the image is acquired when the glare artifact 317 is in registration with the predefined location 330. In this configuration, also shown in solid lines in the side view of the imaging device 300, the image sensor is substantially normal to a statistically relevant number of points in the region of interest 328. In all of the remaining scenes 312, 314 and 318, the glare artifacts 313, 315 and 319 are not in registration with the preferred location 330. Accordingly, the image sensor does not record an image when the sample 322 is in these orientations because the ideal angular orientation of the image sensor is not present. After an image is acquired, the measurement data may then be derived from the region of interest 328 of that image.

As will be appreciated, the above first alternative embodiment may be modified so that the imaging device moves relative to a stationary sample. This modified system also would operate under the principles of the above process.

V. Second Alternative Embodiment

The second alternative embodiment of the invention is also explained with reference to FIG. 9. The imaging device 300 operates under the same principles as described in reference to the first alternative embodiment above; however, instead of waiting to acquire an image when the processor 360 detects registration of a measured glare artifact 317, e.g., the orientation shown in scene 316, the microprocessor stores and records images for multiple scenes, here, each different scene 312, 314, 316 and 318. These recorded images are reviewed by the processor or an operator to select the image having the best glare positioning, i.e., image 316 having glare artifact 317 in registration with preferred location of the glare artifact 330. Measurement data may then be derived from the region of interest 328 of the selected image and the other images discarded.

As in the second alternative embodiment above, the process of this embodiment may be effectively used where the imaging device 300 moves relative to a fixed sample 322.

VI. Third Alternative Embodiment

Figure 10:
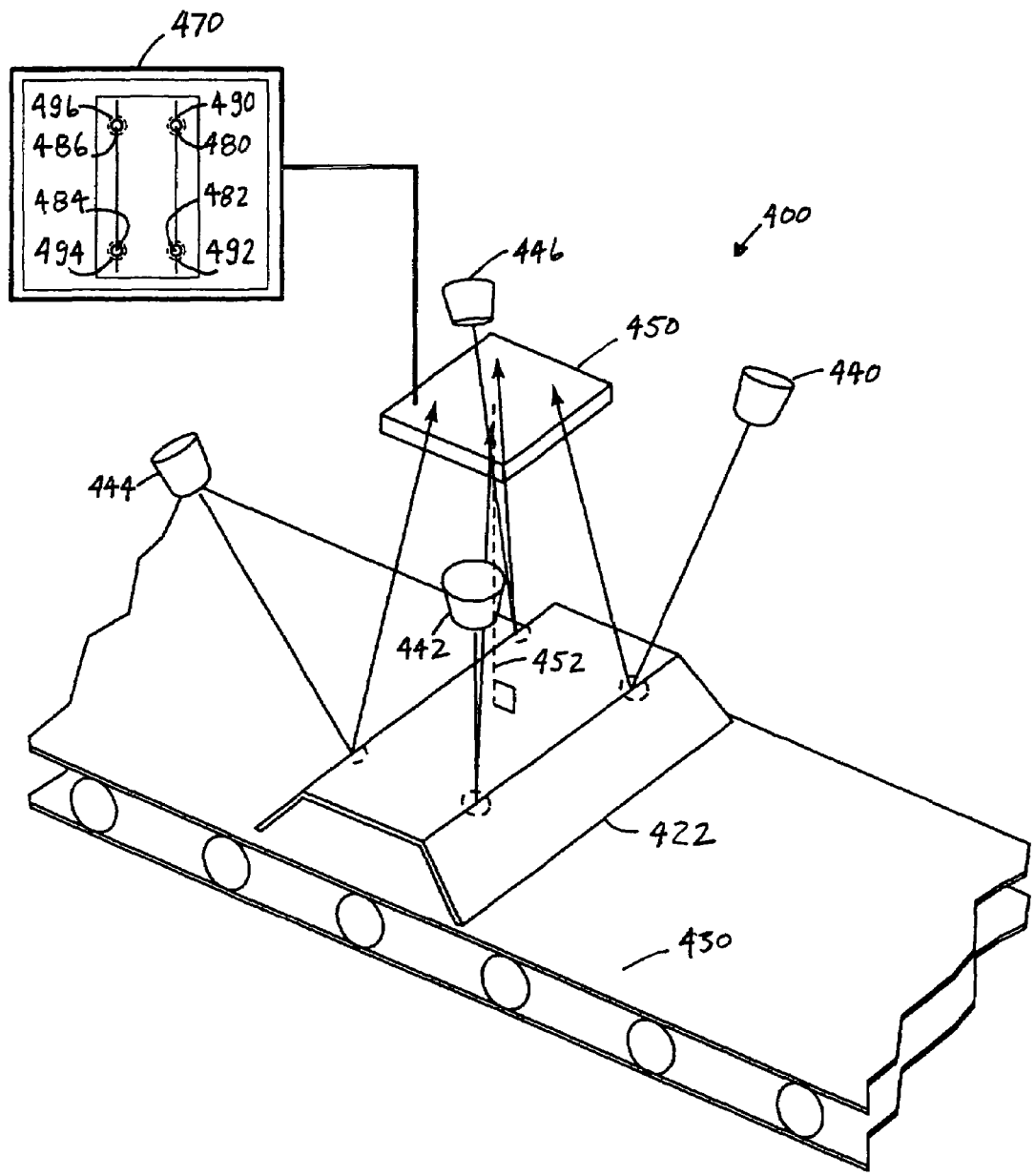
FIG. 10 shows a perspective view of a third alternative embodiment of the imaging device of the present invention including multiple illumination sources.

A third alternative embodiment 400 of the invention is illustrated in FIG. 10. Imaging device 400 is generally identical to the physical construction of imaging device 300 with the exception that multiple, directional illumination sources 440, 442, 444 and 446 are included in the device. Moreover, the sample 422 is of a different shape from sample 322. With the additional illumination sources, many more glare artifacts are created and detected by the image sensor 450. These multiple glare artifacts may be used to more positively confirm that the optical axis 452 is normal to a desired region of interest on the surface of the sample.

As shown, the glare created by the multiple illumination sources is detected by the image sensor 450 and output as multiple glare artifacts 480, 482, 484 and 486 on the display 470. By ensuring that these glare artifacts register with predefined glare artifact locations 490, 492, 494 and 496, respectively, a user or the system may positively confirm that the ideal angular orientation is established between the image sensor 450 and a region of interest on the surface of the sample 422.

Given multiple illumination sources, it may be difficult to associate one illumination source with a particular glare artifact. Several options are available to solve this problem. For example, each illumination source 440, 442, 444 and 446 may be appropriately modulated in intensity differentiate each in time. As another example, each source 440, 442, 444 and 446 may be of a different color or spectral composition. Both examples provide a way to reduce confusion among glare artifacts. These and other techniques-may also be applied to the other embodiments herein as desired.

VII. Fourth Alternative Embodiment

Figure 11:
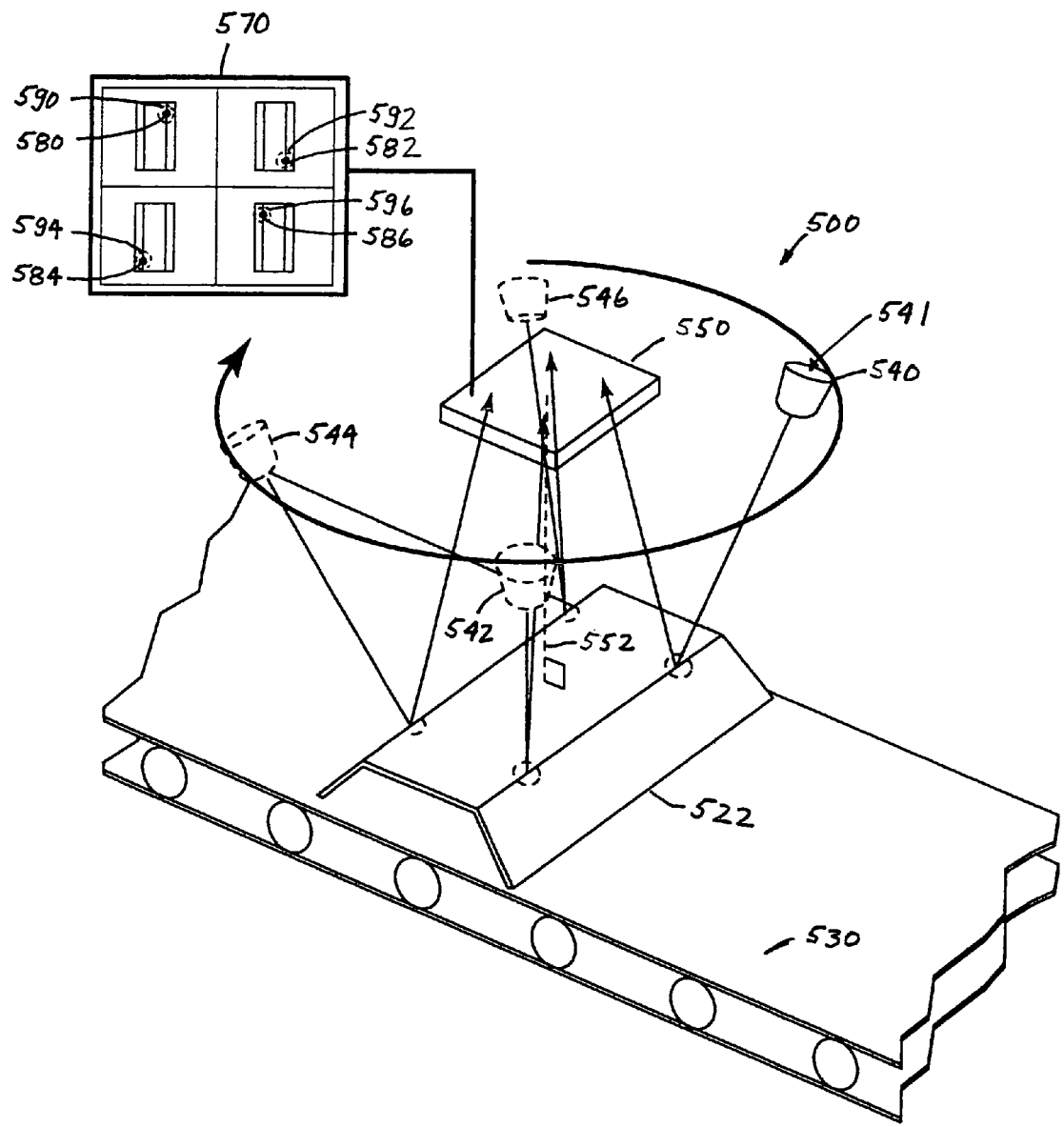
FIG. 11 shows a perspective view of a fourth alternative embodiment of the imaging device of the present invention including a time varying illumination source.

A fourth alternative embodiment 500 of the invention is shown in FIG. 11. The imaging device 500 is generally identical to the imaging device 400, with the exception that instead of having multiple illumination sources, imaging device 500 includes one illumination source 541 that is moved to multiple positions 540, 542, 544 and 546 to vary its angular relationship relative to the image sensor 550 and sample 522 over time. Consequently, a larger number of glare artifacts may be measured and compared to predefined glare artifact locations to ensure accurate angular orientation of the imaging device 500 relative to the sample 522.

The output of glare detected by the image sensor 550 on the display 570 is also similar to that of the display 470 of the third alternative embodiment, except that a different image is generated for each different location 540, 542, 544 and 546 of the illumination source 541. As with the third alternative embodiment, by ensuring the glare artifacts 580, 582, 584 and 586 substantially register with predefined locations 590, 592, 594 and 596, respectively in each respective image, a user can confirm the ideal angular orientation is established between the image sensor 550 and a region of interest to the surface of the sample 522.

The illumination source need not move in a circular, time-varying path, but may optionally move in any time-varying angular relationship relative to the image sensor 550, the sample 522, or both, that is conducive to generating multiple glare artifacts in an image of a sample. Moreover, additional time-varying illumination sources may be added as desired.

The present invention provides a system and method for acquiring a desired angular orientation of an imaging device relative to a sample to ensure that measurements of the sample are accurately and consistently captured. The real-time steering and visual confirmation of ideal adjustment, using the relative positioning of glare artifacts within an image, eliminates the guess-work associated with orienting an imaging device for a measurement. Although the imaging device of the present invention has been disclosed in connection with dental and manufacturing applications, the invention is applicable to virtually any reflectance characteristic measurement instrument using any reflectance characteristic measurement technology. Further, although the invention has been described in connection with generally glossy materials, which generate specular reflections, the invention is applicable to measurement of matte-finish objects which generate diffuse specular reflections and hybrids of matte-finish objects and glossy objects.

The above descriptions are those of the preferred embodiments of the invention. Various alterations and changes can be made without departing from the spirit and broader aspects of the invention as defined in the appended claims, which are to be interpreted in accordance with the principles of patent law including the Doctrine of Equivalents. Any references to claim elements in the singular, for example, using the articles "a," "an," "the," or "said," is not to be construed as limiting the element to the singular.

The embodiments of the invention in which an exclusive property or privilege is claimed are defined as follows:

1. A method for adjusting an imaging device that includes an image sensor relative to an object comprising: locating the image sensor of the imaging device relative to the object; illuminating the object to create glare; detecting the glare with the image sensor; and adjusting a position of the image sensor relative to the object based on a relationship between a present position of the detected glare relative to the object and a desired position of the glare relative to the object.

2. The method of claim 1 comprising displaying the glare to a user on a display.

3. The method of claim 2 wherein the imaging device instructs the user to perform said adjusting.

4. The method of claim 3 wherein the display displays arrows to direct a user in said adjusting.

5. The method of claim 2 comprising highlighting the glare on the display.

6. The method of claim 1 wherein said illuminating is performed with a source at a position distanced from the object and the image sensor, and wherein the position is time-varied relative to at least one of the image sensor and the object.

7. The method of claim 1 wherein the object is at least one of a human tooth and a shade guide tab, including a cervical edge and an incisal edge, the cervical edge disposed a distance from the incisal edge.

8. The method of claim 7 wherein the position of the image sensor is adjusted relative to the at least one of a human tooth and a shade guide tab to ensure that the glare is located at a predefined position relative to the at least one of a human tooth and a shade guide tab.

9. The method of claim 1 comprising repeating said aforementioned steps to identify a desired location of the glare in an image, the desired location corresponding to an optimal angular orientation of the imaging device relative to the object.

10. A method for steering an imaging device disposed in a first orientation relative to an object, the object illuminated such that a glare artifact is visible in a first location on the object, comprising: sensing the glare artifact; and providing instructions to move the glare artifact to a second location on the object based on said sensing, whereby the imaging device is adjusted to a second orientation relative to the object.

11. The method of claim 10 wherein the instructions are provided to a user.

12. The method of claim 11 where the imaging device includes a display and the instructions are provided to the user via an arrow on the display.

13. The method of claim 10 wherein the detected glare artifact is displayed in an image including at least a portion of the object.

14. The method of claim 13 comprising highlighting the glare artifact in the first location.

15. The method of claim 14 comprising indicating when the glare artifact is in the second location.

16. The method of claim 10 wherein the object includes a non-planar surface.

17. The method of claim 16 wherein the second location substantially corresponds to one-third of the distance away from the cervical edge of the tooth.

18. The method of claim 10 wherein the object is at least one of a human tooth and a shade guide tab including a cervical edge, an incisal edge, and a region representative of the reflectance characteristics of the at least one of a human tooth and a shade guide tab, the cervical edge disposed a distance from the incisal edge, and wherein the imaging device includes an image sensor having an optical axis.

19. The method of claim 18 wherein the second orientation provides alignment of the optical axis so that the optical axis is substantially normal to the region.

20. A method for attaining a desired angular orientation of an imaging device relative to an object, the method comprising: sensing the object and a glare artifact associated with the object; determining a position of the glare artifact relative to the object; and determining the desired angular orientation based on the determined position of the glare artifact.

21. The method of claim 20, wherein said determining a position of the glare artifact includes defining a boundary of an image of the object.

22. The method of claim 20, wherein said determining the desired angular orientation includes comparing the determined position of the glare artifact to a preferred position of the glare artifact.

23. The method of claim 20, further comprising illuminating the object.

24. The method of claim 20, further comprising displaying an image of the object.

25. The method of claim 24, wherein said displaying the image includes highlighting an area associated with the glare artifact.

26. The method of claim 20, further comprising generating an instruction to adjust the angular orientation of the imaging device.

27. The method of claim 20, further comprising adjusting the angular orientation of the imaging device.

28. The method of claim 27, wherein said adjusting the angular orientation of the imaging device includes aligning an optical axis of an image sensor of the imaging device substantially normal to a surface of the object.

29. The method of claim 20, further comprising measuring a characteristic of the object.

* * * * *